(12) United States Patent
Schwarz et al.

(10) Patent No.: US 7,211,430 B2
(45) Date of Patent: May 1, 2007

(54) SYSTEM FOR STIRRING GROWTH MEDIUM

(75) Inventors: Daniel L. Schwarz, Timonium, MD (US); Paul Hansen, Hampstead, MD (US); Frederick Pierre Dimpfel, Foresthill, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/921,542

(22) Filed: Aug. 3, 2001

(65) Prior Publication Data

US 2003/0031089 A1 Feb. 13, 2003

(51) Int. Cl.
*B01F 13/08* (2006.01)
(52) U.S. Cl. .................... 435/302.1; 366/273
(58) Field of Classification Search ................ 366/273, 366/274; 435/302.1
See application file for complete search history.

(56) References Cited

U.S. PATENT DOCUMENTS

| | | | | |
|---|---|---|---|---|
| 1,242,493 | A | * | 10/1917 | Stringham ................... 366/274 |
| 1,928,382 | A | * | 9/1933 | Koster ......................... 148/102 |
| 2,350,534 | A | * | 6/1944 | Rosinger |
| 2,974,018 | A | * | 3/1961 | McNeilly ................. 422/82.05 |
| 2,999,673 | A | * | 9/1961 | Kessler ..................... 366/162.1 |
| 3,328,255 | A | * | 6/1967 | Ilg |
| 3,356,346 | A | * | 12/1967 | Landsberger ............... 366/274 |
| 3,905,865 | A | * | 9/1975 | McAleer et al. |

(Continued)

FOREIGN PATENT DOCUMENTS

DE 839 269 * 5/1952

OTHER PUBLICATIONS

Lufburrow, Robert A., "Inverse-Square Law Experiment", 1963, American Journal of Physics, vol. 31, pp. 60-62.*
Castaner et al., "The Magnetic Dipole Interaction as Measured by Spring Dynamometers", 2006, American Journal of Physics, vol. 74, pp. 510-513.*

*Primary Examiner*—David Sorkin
(74) *Attorney, Agent, or Firm*—Mark Lindsey; Bruce S. Weintraub

(57) ABSTRACT

An improved system and method for stirring suspended solids in a liquid media to enhance sample growth and improve sample detection results. The system and method employs a sample vessel holder which adapted to receive at least one sample vessel which contains the solids and liquid media and a stirrer, such as a ferrous metal filled stirrer, and maintain the sample vessel in a position such that the longitudinal axis of the sample vessel extends at an angle substantially less than 90 degrees with respect to the horizontal, such as within the range of about 15 degrees to about 25 degrees with respect to the horizontal. The system and method further employs a magnet driver, adapted to move a magnet, such as a rare earth magnet, proximate to an outer surface of the sample vessel to permit the magnet to impose a magnetic influence on the stirrer to move the stirrer in the sample vessel. Specifically, the magnet driver is adapted to move and, specifically, rotate the magnet such that the magnetic influence moves the stirrer along a side wall of the sample vessel. The magnet driver is further adapted to move the magnet away from said outer surface of the sample vessel to allow gravity to move the stirrer toward the bottom of the sample vessel. This technique therefore provides a more gentle and controlled stirring of the suspended solution.

9 Claims, 10 Drawing Sheets

U.S. PATENT DOCUMENTS

| | | | |
|---|---|---|---|
| 4,040,605 A | 8/1977 | Towsend | |
| 4,152,213 A | 5/1979 | Ahnell | |
| 4,266,950 A * | 5/1981 | Makino et al. | |
| 4,477,192 A | 10/1984 | Bonney | |
| 4,483,623 A | 11/1984 | Eaton et al. | |
| 4,889,992 A | 12/1989 | Hoberman | |
| 4,911,555 A | 3/1990 | Saffer et al. | |
| 4,945,060 A | 7/1990 | Turner et al. | |
| 5,094,955 A | 3/1992 | Calandra et al. | |
| 5,120,135 A * | 6/1992 | Ullman | |
| 5,155,019 A | 10/1992 | Sussman et al. | |
| 5,164,796 A | 11/1992 | Di Guiseppi et al. | |
| 5,217,876 A | 6/1993 | Turner et al. | |
| 5,310,658 A | 5/1994 | Berndt | |
| 5,567,598 A | 10/1996 | Stitt et al. | |
| 5,586,823 A | 12/1996 | Carr | |
| 5,856,175 A | 1/1999 | Thorpe et al. | |
| 5,863,752 A | 1/1999 | Court et al. | |
| 5,918,093 A * | 6/1999 | Kim | |
| 5,961,213 A | 10/1999 | Tsuyuki et al. | |
| 6,095,677 A * | 8/2000 | Karkos, Jr. et al. | |
| 6,153,400 A | 11/2000 | Matsumura et al. | |
| 6,251,624 B1 | 6/2001 | Matsumura et al. | |
| 6,467,946 B1 * | 10/2002 | Gebrian | |
| 6,537,801 B1 | 3/2003 | Ida et al. | |
| 2002/0118594 A1 * | 8/2002 | Vellinger et al. | 366/116 |
| 2002/0197708 A1 | 12/2002 | Bachur, Jr. | |
| 2003/0031089 A1 | 2/2003 | Schwarz et al. | |
| 2003/0111607 A1 | 6/2003 | Bachur, Jr. et al. | |

\* cited by examiner

SYSTEM FOR STIRRING GROWTH MEDIUM

BACKGROUND OF THE INVENTION

1. Field of the Invention

The present invention relates to an improved system and method for stirring suspended solids in a liquid media. More particularly, the present invention relates to a system and method employing a stirrer, in particular, a magnetic ferrous metal-filled polymer, which is deposited in a vessel containing a liquid media that includes a suspended solid, and is manipulated by a moving magnet outside the vessel to stir the suspended solid in an optimal manner.

2. Description of the Related Art

Many medical diagnoses require that a fluid sample, such as a blood sample, be taken from a patient, cultured in a growth medium, and then examined for the presence of a pathogen believed to be causing the patient's illness. The growth medium provides nutrients that allow the pathogen, such as bacteria, virus, mycobacteria, mammalian cells or the like, to multiply to a sufficient number so that their presence can be detected.

In some cases, the pathogen can multiply to a large enough number so that it can be detected visually. For example, a portion of the culture can be placed on a microscope slide, and visually examined to detect for the presence of a pathogen of interest.

Alternatively, the presence of a pathogen or other organism can be detected indirectly by detecting for the presence of byproducts given off by the microorganism during its growth. For example, certain microorganisms such as mammalian cells, insect cells, bacteria, viruses, mycobacteria and fungi consume oxygen during their growth and life cycle. As the number of microorganisms increases in the sample culture, they naturally consume more oxygen. Furthermore, these oxygen consuming organisms typically release carbon dioxide as a metabolic byproduct. Accordingly, as the number of organisms present increases, the volume of carbon dioxide that they collectively release likewise increases.

Alternatively, instead of detecting for the presence of carbon dioxide to detect the presence of an oxygen consuming microorganism, it is possible to detect for a depletion in the concentration of oxygen in the sample of interest. The presence of oxygen consuming organisms can also be detected by detecting for a change in pressure in a sealed sample vial containing the sample of interest. That is, as oxygen in a closed sample vial is depleted by oxygen consuming organisms, the pressure in the sealed sample vial will change. The pressure will further change in the sample vial as the organisms emit carbon dioxide. Therefore, the presence of such organisms can be detected by monitoring for a change in pressure in the closed sample vial.

Several methods exist for detecting the presence of carbon dioxide in a sample to determine whether organisms are present in the sample. For example, an instrument known as the BACTEC® 9050 manufactured by Becton Dickinson and Company detects for the change in color of an indicator to determine whether carbon dioxide is present in a sample. That is, each sample is collected in a respective sample vial containing an indicator medium having a chemical that reacts in the presence of carbon dioxide to change color. A light sensor detects the color of the indicator medium in the sample vial when the sample vial is loaded into the instrument. If the sample contains an organism which emits carbon dioxide, the reflected or fluorescent intensity of the indicator medium will change in response to the presence of carbon dioxide. The light sensor will therefore detect this change in intensity, and the instrument will thus indicate to an operator that an organism is present in the sample contained in the sample vial. Other examples of instruments for detecting the presence of organisms in a sample by detecting for the change in carbon dioxide in the sample are described in U.S. Pat. Nos. 4,945,060, 5,164,796, 5,094,955 and 5,217,876, the entire contents of each of these patents are incorporated herein by reference.

An instrument employing an oxygen detecting technique is described in U.S. Pat. No. 5.567,598, the entire content of which is incorporated herein by reference. Instruments that are capable of detecting changes in pressure in the sample vial are described in U.S. Pat. Nos. 4,152,213, 5,310,658, 5,856,175 and 5,863,752, the entire contents of each of these patents are incorporated herein by reference. In addition, an instrument capable of detecting changes in carbon dioxide concentration, changes in oxygen concentration, and changes in pressure in the vessel is described in a U.S. patent application of Nicholas R. Bachur et al. entitled "System and Method for Optically Monitoring the Concentration of a Gas, or the Pressure, in a Sample Vial to Detect Sample Growth", Ser. No. 09/892,061, filed on Jun. 26, 2001, and another instrument capable of detecting changes in carbon dioxide concentration or changes in oxygen concentration in the vessel is described in a U.S. patent application of Nicholas R. Bachur et al. entitled "System and Method for Optically Monitoring the Concentration of a Gas in a Sample Vial Using Photothermal Spectroscopy to Detect Sample Growth", Ser. No. 09/892,012, filed on Jun. 26, 2001, the entire contents of both of said applications being incorporated herein by reference.

It is noted that the results obtained by organism detection techniques described above can be improved if the growth of the organism is enhanced to cause a greater production of carbon dioxide, a greater depletion of oxygen, and a greater change in pressure in the vessel. It is known that the biological activity of a solid sample in a liquid media can be enhanced by maintaining the solid sample in a suspended state. This can be accomplished by continuously stirring the solid-liquid mixture, which improves nutrient, waste and gas exchange in the mixture.

Examples of stirring techniques are described in U.S. Pat. Nos. 5,586,823, 4,483,623 and 4,040,605, the entire contents of each are incorporated herein by reference. Each of these techniques employs a magnetic stirrer that is placed in the vessel containing the sample and manipulated by a magnet to stir the sample in the vessel.

Although these stirring techniques may be somewhat effective in enhancing sample growth, they each suffer from certain disadvantages. For example, because each of the techniques require that the vessel be maintained in a vertical configuration, the fluid-gas interface is minimized, especially in vessels that are not shallow. This minimal fluid-gas interface inhibits biological performance in the vessel.

In addition, the vertical configuration of the vessel allows for the magnets to lose their influence over the magnetic stirrer in the vessel, especially if the magnetic influence on the stirrer is weak as in the case of gentle stirring. Also, the vertical configuration causes the stirrer in the vessel to follow a semi-random stirring path, which results in a stirring action that is inefficient and potentially damaging to the sample. Furthermore, in order to change the intensity of the stirring in these known arrangements, the physical size of the stirrer or the apparatus needs to be changed.

A need therefore exists for an improved system and method for stirring suspended solids in a liquid media to enhance sample growth and thus improve sample detection results.

SUMMARY OF THE INVENTION

An object of the present invention is to provide an improved system and method for stirring suspended solids in a liquid media to enhance sample growth and improve sample detection results.

Another object of the present invention is to provide an improved system and method for stirring suspended solids in a liquid media which is capable of changing stirring intensity without changing the size of the stirrer in the media or the size or operation of the system.

These and other objects are substantially achieved by providing a system and method for stirring a solid suspended in a liquid in a sample vessel that includes a stirrer, such as a ferrous material filled polymer stirrer. The system and method employs a sample vessel holder which adapted to receive at least one sample vessel and maintain the sample vessel in a position such that the longitudinal axis of the sample vessel extends at an angle substantially less than 90 degrees with respect to the horizontal, such as within the range of about 15 degrees to about 25 degrees with respect to the horizontal. The system and method further employs a magnet driver, adapted to move a magnet, such as a rare earth magnet, proximate to an outer surface of the sample vessel to permit the magnet to impose a magnetic influence on the stirrer to move the stirrer in the sample vessel. Specifically, the magnet driver is adapted to move the magnet such that the magnetic influence moves the stirrer along a side wall of the sample vessel. The magnet driver is further adapted to move the magnet away from said outer surface of the sample vessel to allow gravity to move the stirrer toward the bottom of the sample vessel. The magnet driver device can comprise a magnet shaft assembly having a magnet coupled thereto, and a motor, adapted to move the magnet shaft assembly to move the magnet proximate to the outer surface of the sample vessel and away from the outer surface of the sample vessel. The magnet shaft assembly can be rotatable, and the motor rotates the magnet shaft assembly to move the magnet proximate to the outer surface of the sample vessel and away from the outer surface of the sample vessel. The motor can be directly or magnetically coupled to the magnet shaft assembly. Additionally, the sample vessel holder can be adapted to receive a plurality of the sample vessels and maintain each of the sample vessels in a respective position such that the longitudinal axis of each sample vessel extends at a respective angle substantially less than 90 degrees with respect to the horizontal. Furthermore, the magnet driver can be adapted to move each of a plurality of magnets proximate to an outer surface of a respective one of the sample vessels to permit the magnet to impose a magnetic influence on the stirrer in the respective sample vessel to move the stirrer in the respective sample vessel.

BRIEF DESCRIPTION OF THE DRAWINGS

These and other objects, advantages and novel features of the invention will be more readily appreciated from the following detailed description when read in conjunction with the accompanying drawings, in which.

DETAILED DESCRIPTION OF THE PREFERRED EMBODIMENTS

Figure 1:
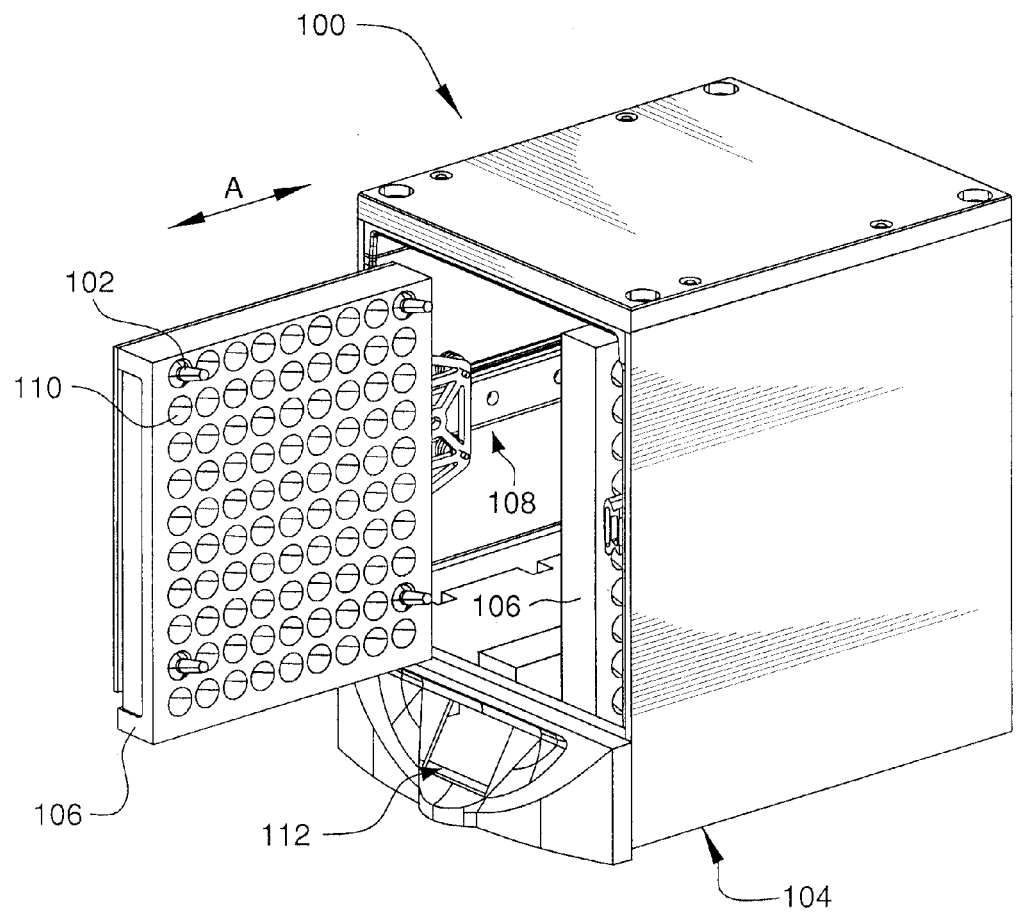
FIG. 1 is a perspective view of an example of a system employing an improved system and method for stirring solid samples suspended in liquid media contained in a plurality of sample vessels according to an embodiment of the present invention.

An example of an incubation and measurement module 100 employing a system for stirring solid samples suspended in liquid media contained in sample vessels 102 according to an embodiment of the present invention is shown in FIG. 1. Further details of the system 100 and the stirring system are shown in FIGS. 2–9. As illustrated, the incubation and measurement module 100 in this example includes a housing 104 and two panels 106 that can be slid into and out of the housing 104 along respective rail arrangements 108 in a direction along arrow A.

Each panel 106 includes a plurality of openings 110, each of which is adapted to receive a sample vessel 102. As discussed in more detail below, each vessel 102 includes a solid sample suspended in a liquid media, and a stirrer. The openings 110 are tilted with respect to the horizontal so that the sample vessels 102 received in the openings 110 are also tilted for reasons discussed in more detail below. In this example, the openings 110 are tilted at 15° or about 15° with respect to the horizontal, so that the sample vessels 102 received in the openings 110 are also tilted at 15° or about 15° with respect to the horizontal. As discussed in more detail below, this tilting creates a large air to liquid interface in the sample vessels 102. Furthermore, the openings 110 and hence the sample vessels 102 need not be tilted at 15° with respect to the horizontal, but rather, can be tilted at an angle within the range of at or about 15° to at or about 25°, with the range of at or about 15° to at our about 20° being preferred. However, the openings 110 and the sample vessels 102 can be tilted at any practical angle with respect to the horizontal that will create a sufficient air to liquid interface.

The openings 110 are arranged in a plurality of rows and columns as shown, and each panel 106 can have any practical number of openings. For example, the openings 110 can be arranged in ten rows and nine columns, thus totaling 90 openings 110 per panel 110. The incubation and measurement module 100 further includes one or more doors (not shown) for closing the housing 104 after the panels 106 have been received in the housing 104.

When a sample culture is to be analyzed by the incubation and measurement module 100, the sample culture is placed in a sample vessel 102, and the sample vessel 102 is loaded into a respective opening 110 in a respective panel 106 in the incubation and measurement module 100. The sample vessel 102 is a closed sample vial in this example. The incubation and measurement module 100 can further include a keyboard 112, a barcode reader (not shown), or any other suitable interface that enables a technician to enter information pertaining to the sample into a database stored in a memory in the incubation and measurement module 100, or in a computer (not shown) which is remote from the module 100 and controls operation of the module 100. The information can include, for example, patient information, sample type, the row and column of the opening 110 into which the sample vessel 102 is being loaded, and so on. The module 100 can include the type of detecting devices as described in U.S. patent applications Ser. Nos. 09/892,061 and 09/892,012, referenced above.

Figure 4:
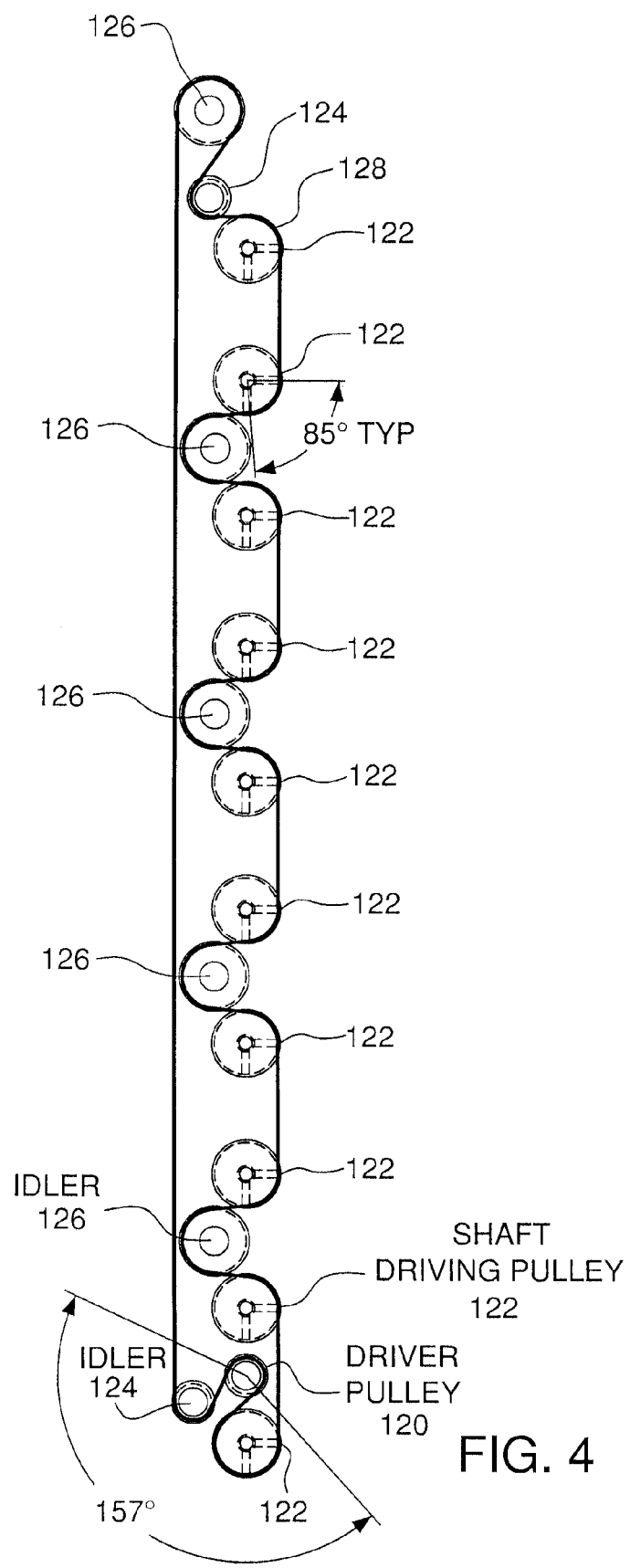
FIG. 4 is a diagrammatic view of a belt and pulley arrangement employed in the panel shown in FIG. 2.

As further shown in FIGS. 2–8, each panel 106 includes a drive assembly 114 for driving a plurality of magnet shaft assemblies 116 as described in more detail below. The drive assembly 114 includes a drive motor assembly 118 and a pulley arrangement comprising a drive pulley 120, shaft driving pulleys 122, idler pulleys 124 and 126, and a serpentine belt 128 that passes around the drive pulley 120, shaft driving pulleys 122, and idler pulleys 124 and 126 as shown in FIG. 4. The drive motor assembly 118 includes a drive motor 130 that is controlled by, for example, a controller 132, such as a microcontroller or the like. The drive shaft 134 of the drive motor 130 is coupled to a magnet plate 136 as shown in detail in FIG. 8. The magnet plate 136 includes a plurality of magnets 138, which are generally strong magnets such as rare earth magnets. The drive motor 130 is mounted inside the housing 104 by, for example, a mounting bracket 140.

Figure 2:
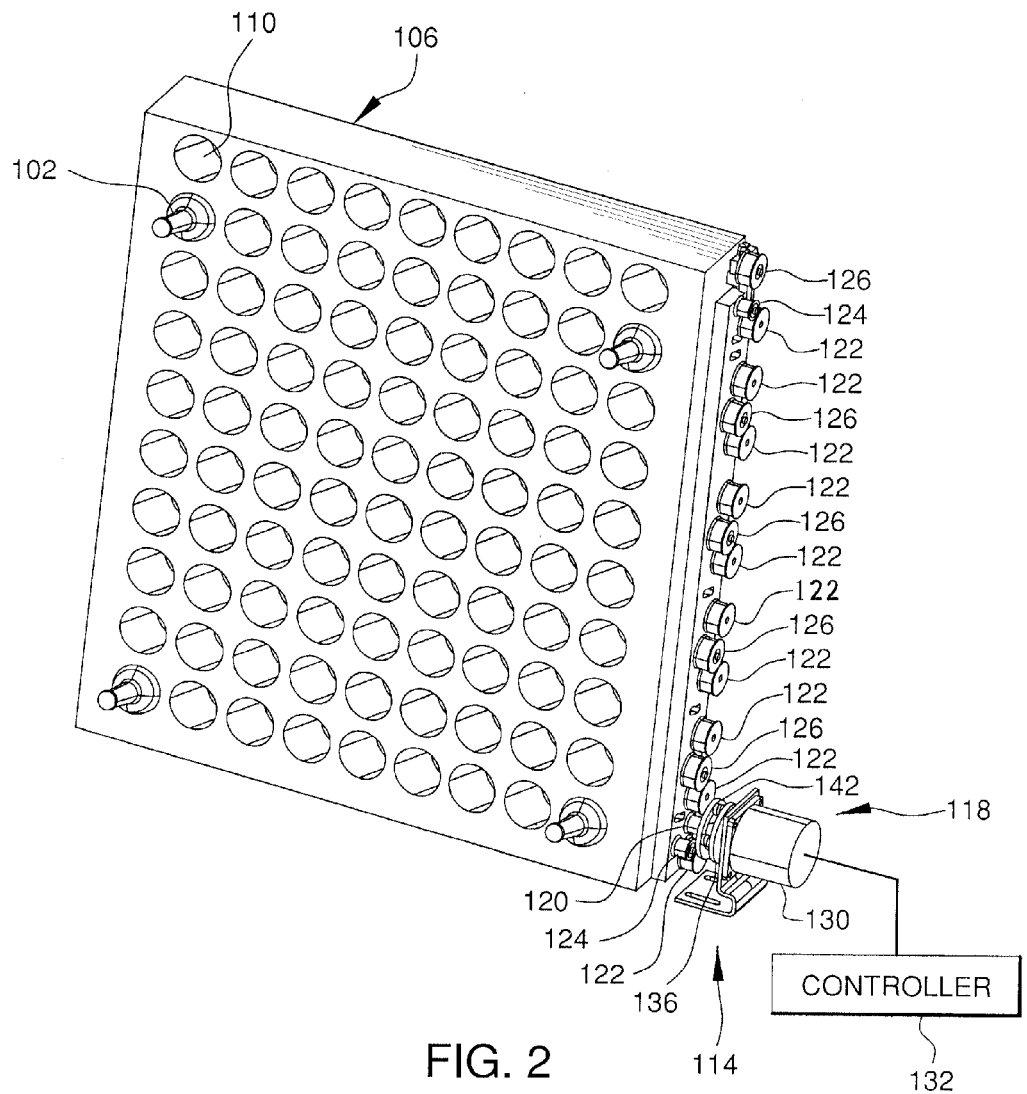
FIG. 2 is a detailed perspective view of an example of a panel in the system shown in FIG. 1 for housing sample vessels.
Figure 3:
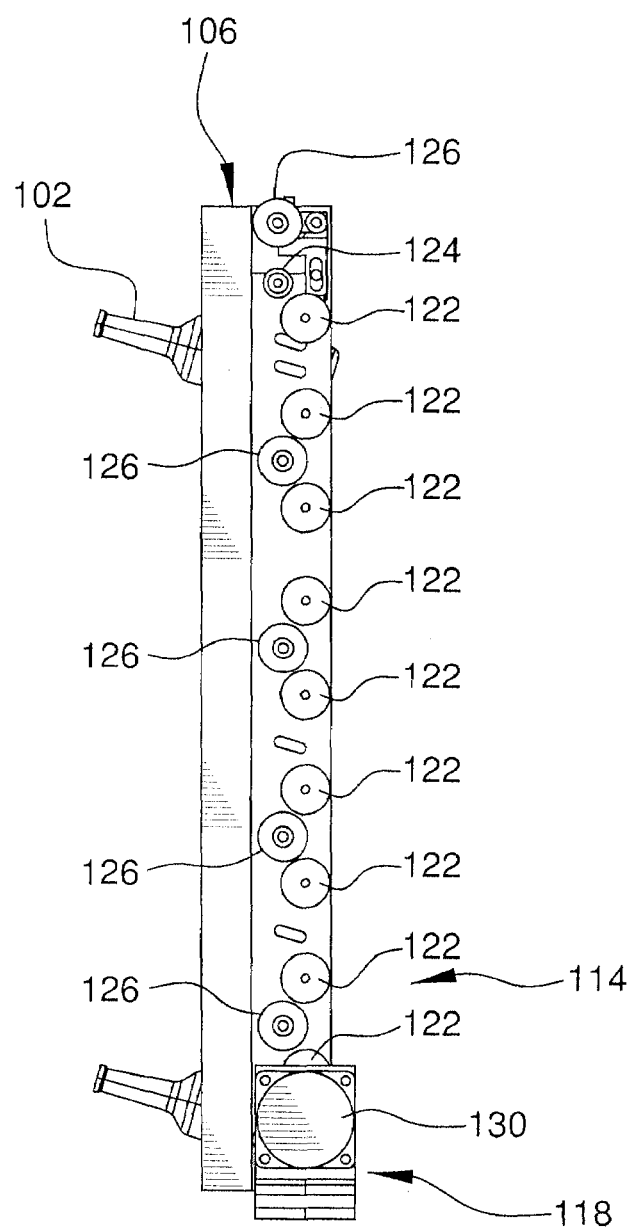
FIG. 3 is a side view of the panel shown in FIG. 2.
Figure 6:
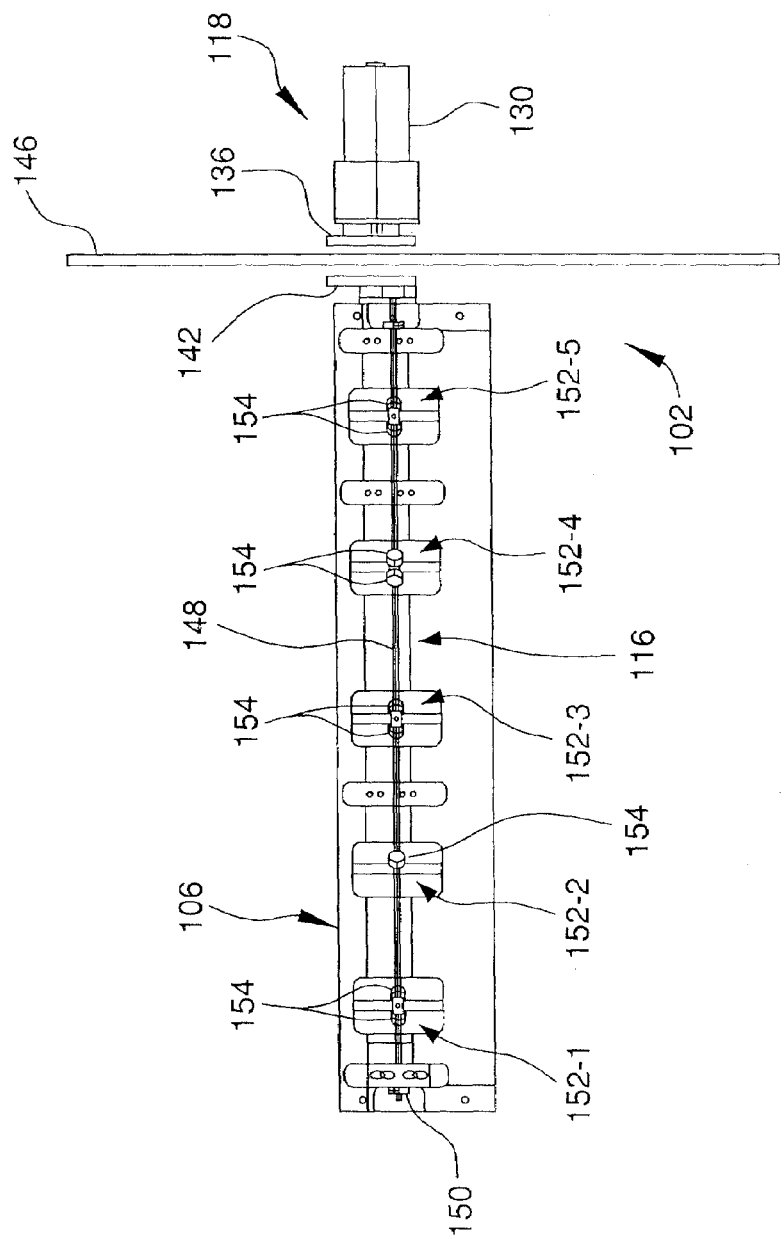
FIG. 6 is a bottom view of the panel shown in FIG. 2.
Figure 7:
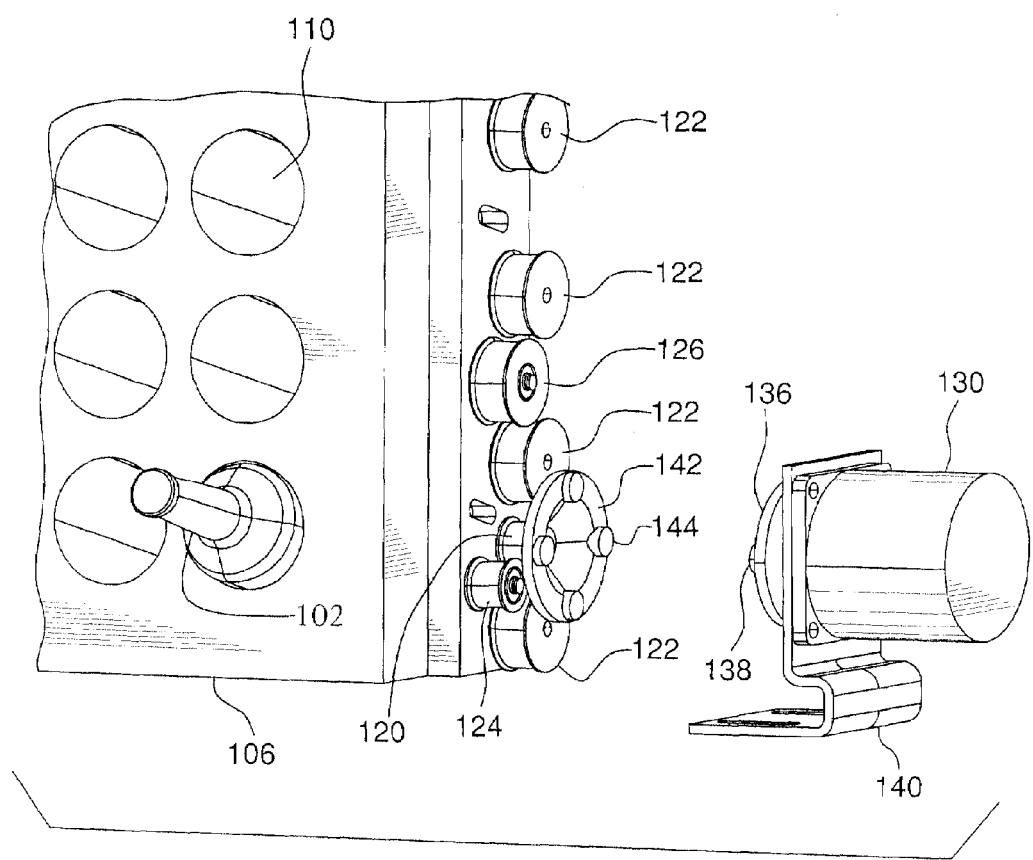
FIG. 7 is a detailed exploded view of the drive arrangement of the panel shown in FIG. 2.
Figure 8:
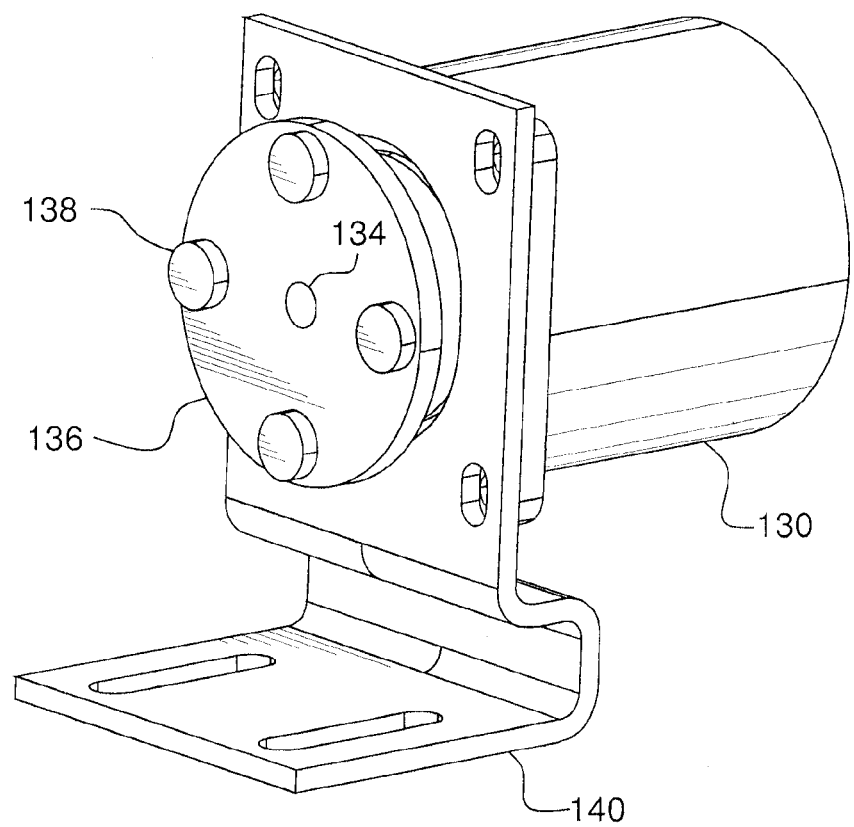
FIG. 8 is a detailed view of the motor of the drive arrangement shown in FIG. 7.

As shown in detail in FIGS. 2 and 7, a magnet plate 142 having a plurality of strong magnets 144 such as rare earth magnets is coupled to drive pulley 120. The drive motor 130 is positioned inside housing 104 so that when its corresponding panel 106 is fully inserted in the housing 104, magnet plate 142 aligns with or substantially aligns with magnet plate 136. It is further noted that the drive motor 130 and magnet plate 136 are located outside of the rear wall 146 of the incubation chamber that is housed inside housing 104 and receives the panels 106. Accordingly, as shown in FIG. 6, magnet plate 136 and magnet plate 142 are on opposite sides of the rear wall 146 of the incubation chamber. However, the magnets 138 and 144 on magnet plates 136 and 142 are strong enough to magnetically couple with each other through the rear wall 146 so that when the drive motor 130 rotates magnet plate 136, the magnetic coupling causes the rotation of magnet plate 136 to rotate magnet plate 142. The rotation of magnet plate 142 drives drive pulley 120, which drives the serpentine belt 128 to drive shaft driving pulleys 122 and idler pulleys 124 and 126. It is noted that by locating drive motor 130 outside of the incubation chamber, the heat emitted by drive motor 130 during operation does not influence the temperature within the incubation chamber. Furthermore, the drive motor 130 is not influence by the heat of the incubation chamber, which can damage the drive motor 130.

Figure 5:
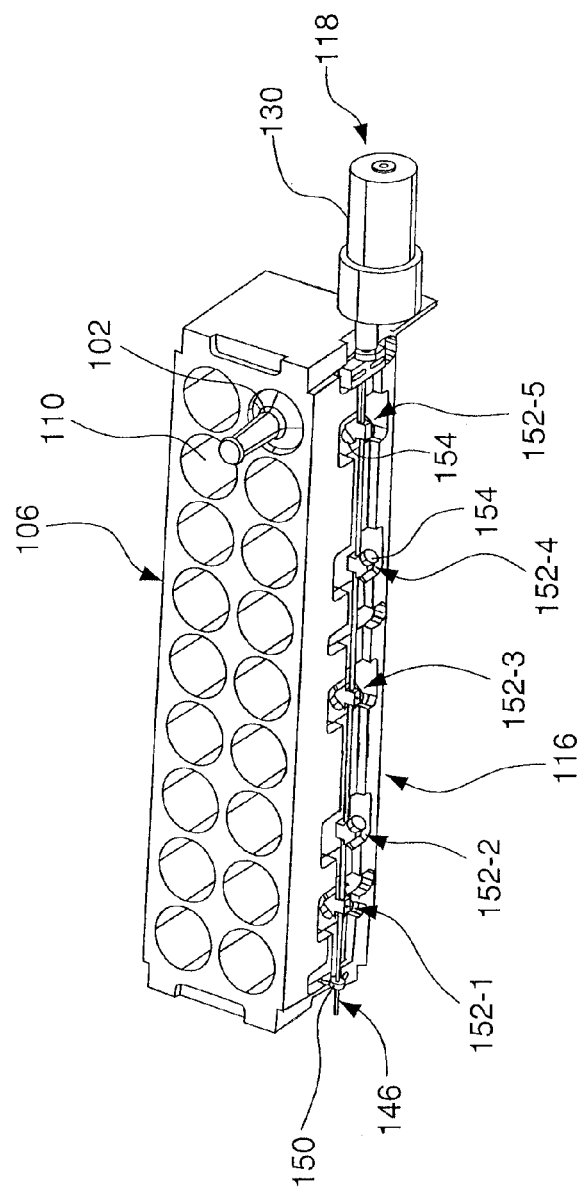
FIG. 5 is a detailed perspective bottom view of the bottom two rows of the panel shown in FIG. 2.

As can be appreciated from FIGS. 2–7 and, in particular, FIGS. 5 and 6, each of the shaft driving pulleys 122 is coupled to a respective magnet shaft assembly 116. In this example, panel 106 includes ten shaft driving pulleys 122 and ten corresponding magnet shaft assemblies 116, each corresponding to a respective row of openings 110. Each magnet shaft assembly 116 includes a shaft 148 that is coupled at one end to a respective shaft driving pulley 122, extends along the width of the panel 104 and is rotatably coupled at its other end to a mounting assembly 150. A plurality of magnet assemblies 152-1 through 152-5 are coupled to each shaft 148 and rotate in unison with the shaft 148 when the shaft 148 is rotated about its longitudinal axis by its respective shaft driving pulley 122. As shown in FIG. 5, each magnet assembly 152-1 through 152-5 has one or two strong magnets 154, such as rare earth magnets, which can be received into corresponding openings 156-1 through 156-5, respectively, in the panel 106 as the shaft 148 rotates. Specifically, the total number of magnets 154 of a magnet shaft assembly 116 corresponds to the number of openings 110 in the row of openings corresponding to the magnet shaft assembly 116. In this example, magnet shaft assembly 116 includes ten magnets 154 corresponding to the ten openings 110 in the row of openings corresponding to the magnet shaft assembly 116.

It is further noted that the magnet or magnets 154 of adjacent magnet assemblies (e.g., magnet assemblies 152-1 and 152-2) are oriented at 180° or approximately 180° with respect to each other about the shaft 148. That is, when the magnets 154 of magnet assembly 152-1 are positioned outside of opening 156-1, the magnets 154 of magnet assembly 152-2 are positioned inside opening 156-2 as shown in FIGS. 5 and 6. The magnets 154 are arranged in this manner to improve the overall balance of the magnet shaft assembly 116.

Figure 9:
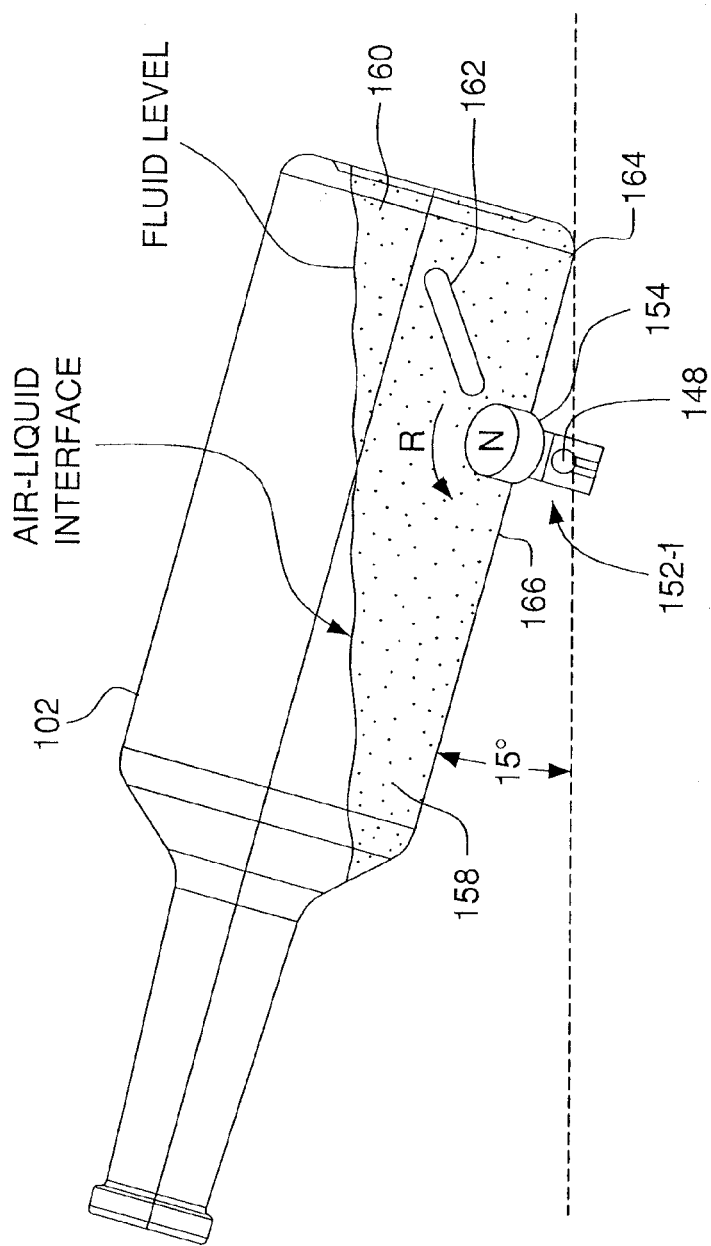
FIG. 9 is a conceptual view showing an example of the relationship between the position and motion of a magnet in the panel show in FIG. 2 and a respective sample vessel containing a stirrer in accordance with an embodiment of the present invention.

The stirring operation performed by the magnet shaft assembly 116 will now be described. FIG. 9 shows an example of the relationship between a magnet 154 of magnet assembly 152-1 and a sample vessel 102 that has been loaded into the opening 110 corresponding to the magnet 154. As discussed above, each magnet 154 corresponds to an opening 110 in the row of openings corresponding to the magnet shaft assembly 116. As shown, when a sample vessel 102 is received in an opening 110, it is tilted with respect to the horizontal at the angle at which the opening 110 is tilted with respect to the horizontal, which is 15° or about 15° in this example. As mentioned above, this tilting creates a significantly large air-liquid interface in the sample vessel 102.

Figure 10:
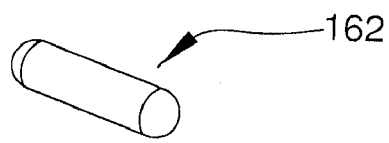
FIG. 10 is a detailed perspective view of an example of a stirrer as shown in FIG. 9.
Figure 11:
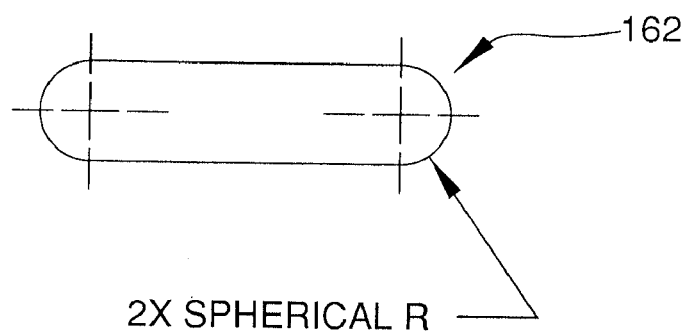
FIG. 11 is a side view of the stirrer shown in FIG. 10.
Figure 12:
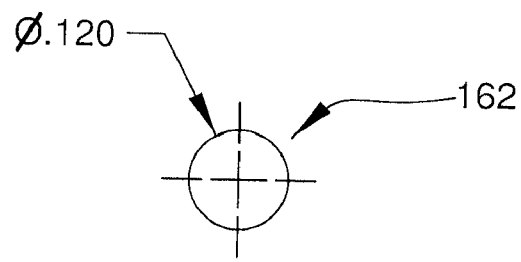
FIG. 12 is a cross-sectional view of the stirrer shown in FIG. 10.

As further discussed above, each sample vessel 102 includes a solid sample 158, such as an organism of the type described above, that is suspended in a liquid media 160, such as a growth media for enhancing growth- of the organism. Each sample vessel 102 further includes a stirrer 162 which is preferably a magnetic, ferrous metal filled polymer. It is noted that the term "magnetic" in this context refers to a type of ferrous metal, such as magnetic stainless steel, that responds to the magnetic fields of the magnet 154. The ferrous material employed in the stirrer according to this embodiment is not itself a magnet, nor is it magnetized. Further details of the stirrer 162 are shown in FIGS. 10–12. The stirrer 162 can be rod shaped or cylindrical as shown, or have any other suitable shape. The stirrer 162 can have an overall length within a range of, for example, 0.500 or about 0.500 inches to 0.750 or about 0.750 inches, and can have an overall diameter of 0.120 or about 0.120 inches.

The stirrer 162 can include about 50% to about 80% of polymer by weight, with the remaining 50% to 20% of the weight being ferrous metal. However, any ratio of polymer to ferrous metal can be used as long as it provides sufficient cohesiveness to hold the stirrer 162 together and to allow sufficient responsiveness to the magnet 154. The polymer material is preferably a biologically inert polymer, such as nylon or polypropylene, which reduces the overall surface hardness of the stirrer 162, and thus reduces potential damage to the solid sample 158 in the suspension as well as to the sample vessel 102. The ferrous material is preferably stainless steel, but can be any suitable material that can respond to magnetic influence from magnet 154. The stirrer 162 can be color coded with colors such as blue, gray, red, green, orange, and so on, to provide an indication of the type and percentage content of the polymer and ferrous material. The stirrer 162 can be provided in the sample vessel 110, or can be added to the sample vessel 110 prior to or after adding the solid sample 158 and liquid media 160 to the sample vessel 110.

As further shown in FIG. 9, the stirring action is created by controlling the motor 130 (see FIGS. 2, 3 and 5–8) to rotate the magnet shaft assembly 116 in a direction R. The rotation of the magnet shaft assembly 116 thus rotates the shaft 148 about it longitudinal axis, which in turn rotates the magnets 154 about the longitudinal axis of the shaft 148. As the magnets 154 rotate, they are brought into their respective openings 156-1 through 156-5 in panel 106 (see FIGS. 5 and 6). That is, when shaft 148 is rotated, magnet 154 of magnet assembly 152-1 cyclically enters opening 156-1 to come proximate to sample vessel 102 in its corresponding opening 110, and exits opening 156-1 to become distant from sample vessel 102. This movement causes a rhythmic agitation of the stirrer 162 to occur. That is, as magnet 154 swipes proximate to the outer surface of sample vessel 102, its magnetic force attracts stirrer 162 to pull stirrer 162 away from the bottom edge 164 of the sample vessel 102 upward along wall 166 of the sample vessel 102. As the magnet 154 begins to rotate away from the sample vessel 102, the stirrer 162 becomes less influenced by the magnetic force of magnet 164, and due to gravity falls along wall 166 of sample vessel 102 toward the bottom edge 164. This movement is repeated each time magnet 154 swipes along the outer surface of sample vessel 102. It is desirable for the magnet 154 to be rotated in the direction R so that the stirrer 162 is first moved up along wall 166 and then allowed to fall back toward the bottom edge 164. Also, the motor 130 can be rotated at a speed of, for example, 150 rotations per minute, which causes the stirrer 162 to travel through the stirring path described above 150 times per minute. However, the motor 130 can be controlled to rotate at any practical speed to achieve the desired stirring action.

It is further noted that by increasing the ferrous fill content of the stirrer 162, the magnetic influence that magnet 154 has on the stirrer 162 will increase. Likewise, by decreasing the ferrous fill content of the stirrer 162, the magnetic influence that magnet 154 has on the stirrer 162 will decrease. Accordingly, the intensity of the stirring can be varied by simply replacing stirrer 162 with a stirrer having a different ferrous fill content Furthermore, the size and shape of the stirrer 162 need not be changed.

The above arrangement provides several advantages over the conventional stirring devices discussed in the Background section above. For example, because the tilted openings 110 maintain the sample vessel 102 at a shallow angle (e.g., 15°) with respect to the horizontal to facilitate maximum exposure of liquid phase to gas phase. This therefore provides an improved dissolved gas exchange as a function of the angle. Furthermore, the angled orientation of the sample vessel 102 increases the probability that the magnet 154 will maintain magnetic influence over the stirrer 162. Also, the stirring action can be gentler than in conventional methods since the path of the stirrer 162 is constrained by the wall 166 of the sample vessel 102. All of these improved characteristics of the stirring system enhances the growth of the sample in the liquid media 160 and thus increases the overall carbon dioxide production, oxygen depletion and pressure variation in the sample vessel 110, thereby improving sample detection results.

Table 1 below shows an example of the sample detection results obtained by agitating various samples according to the embodiments of the present invention discussed above in comparison to the sample detection results obtained by agitating the same types of samples according to a conventional "rocking" method in which the vessel containing the sample is agitated or rocked to thus agitate the sample therein.

TABLE 1

Sample Detection Comparison Data

| Organism and Strain | Magnetic Agitation Time to Detection in Hours | Rocking Agitation Time to Detection in Hours |
| --- | --- | --- |
| Candida glabrata 231 | 62 | >120 |
| Candida glabrata 550 | 58 | >120 |
| Candida glabrata 15545 | 51 | >120 |
| Candida glabrata 66032 | 52 | 112 |
| N. meningitidis 13113 | 47 | >120 |
| S. pneumoniae 6305 | 19 | 21 |

As illustrated, for each type of sample, the duration of time that elapses from the beginning of agitation in accordance with the embodiments described above until a detectable amount of sample has been grown is far less that the duration of time that elapses from the beginning of the conventional "rocking" agitation technique until a detectable amount of sample has been grown. Accordingly, the agitation techniques according to the embodiments of the invention described above are far superior to the conventional rocking technique.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system comprising:
   a plurality of sample vessels, each of the sample vessels comprising a longitudinal axis, a growth medium and a stirrer, the stirrer capable of being influenced by a magnetic force; and
   an incubation and measurement module comprising
      at least one panel comprising a plurality of openings for holding the sample vessels, and
      a magnet driver comprising a plurality of magnets,
   wherein each of the openings corresponds with one of the magnets, wherein the magnet driver is adapted to repeatedly move each magnet proximate to and distant from the surface of a corresponding sample vessel when located in the corresponding opening, and wherein the openings are configured to hold the one or more sample vessels such that the longitudinal axis of the vessels are at an angle of less than 90° with the horizontal, wherein the magnet driver comprises:
a magnet shaft assembly comprising a shaft and a plurality of magnet assemblies,
wherein the plurality of magnet assemblies are coupled to the shaft, the magnet assemblies being discreet components or discreet parts of a single component or a combination thereof,
wherein the magnet assemblies comprise a first magnet coupled to and extending from the shaft at a first angle, and a second magnet coupled to and extending from the shaft at a second angle, and
wherein the first magnet corresponds with a first of the one or more openings and the second magnet corresponds with a second of the one or more openings adjacent to the first of the one or more openings,
wherein the magnet shaft assembly is located in the module such that each of the magnet assemblies is located between two of the sample vessel openings.

2. The system of claim 1, wherein the plurality of openings are arranged in at least one row and at least one column.

3. The system of claim 1, wherein the magnet driver further comprises:
a motor engaged with the shaft to rotate the magnet shaft assembly and move the magnets proximate to the outer surface of the corresponding sample vessel and distant from the outer surface of the corresponding sample vessel.

4. The system of claim 1, wherein upon operation of the magnet driver, the magnetic influence moves the stirrer element along a side wall of the sample vessel.

5. The system of claim 1, wherein the magnet driver and magnets are arranged such that, during a portion of the movement of the magnets, gravity moves the stirrer element toward a bottom of the sample vessel.

6. The system of claim 1, wherein the angle is about 15° to about 25°.

7. The system of claim 1, wherein the sample vessels are sample vials.

8. The system of claim 1, wherein the incubation and measurement module further comprises a housing, and at least one door.

9. The system of claim 1, wherein the magnets of adjacent magnet assemblies are orientated approximately 180° with respect to each other about the shaft.

* * * * *